(12) United States Patent
Winter et al.

(10) Patent No.: US 8,907,115 B2
(45) Date of Patent: Dec. 9, 2014

(54) SYNTHESIS AND CHARACTERIZATION OF FIRST ROW TRANSITION METAL COMPLEXES CONTAINING α-KETO HYDRAZONATE LIGANDS AS POTENTIAL PRECURSORS FOR USE IN METAL FILM DEPOSITION

(71) Applicant: Wayne State University, Detroit, MI (US)

(72) Inventors: Charles H. Winter, Bloomfield Hills, MI (US); Lakmal C. Kalutarage, Detroit, MI (US)

(73) Assignee: Wayne State University, Detroit, MI (US)

( * ) Notice: Subject to any disclaimer, the term of this patent is extended or adjusted under 35 U.S.C. 154(b) by 65 days.

(21) Appl. No.: 13/709,564

(22) Filed: Dec. 10, 2012

(65) Prior Publication Data

US 2014/0161977 A1    Jun. 12, 2014

(51) Int. Cl.
*C07F 15/00* (2006.01)
*C07F 13/00* (2006.01)
*C07F 11/00* (2006.01)
*C23C 16/00* (2006.01)
*C07F 19/00* (2006.01)
*C23C 16/455* (2006.01)

(52) U.S. Cl.
CPC .................................. *C23C 16/455* (2013.01)
USPC ............. 556/45; 556/57; 556/146; 427/248.1

(58) Field of Classification Search
USPC ............................ 556/45, 57, 146; 427/248.1
See application file for complete search history.

(56) References Cited

U.S. PATENT DOCUMENTS

| | | |
|---|---|---|
| 3,562,308 A | 2/1971 | Costa et al. |
| 5,721,014 A | 2/1998 | Fakler et al. |
| 6,020,511 A | 2/2000 | Vaartstra et al. |
| 6,786,936 B2 | 9/2004 | Vaartstra |

(Continued)

FOREIGN PATENT DOCUMENTS

WO       2012/067439 A2    5/2012

OTHER PUBLICATIONS d'Alnoncourt R.N. et al., "The preparation of Cu/Al2O3 catalysts via CVD in a fluidized-bed reactor," Surface and Coatings Technology 201, pp. 9035-904, 2007.

(Continued)

*Primary Examiner* — Porfirio Nazario Gonzalez
(74) *Attorney, Agent, or Firm* — Brooks Kushman P.C.

(57) ABSTRACT

A compound that is useful for forming a metal by reaction with a reducing agent is described by formula (I):

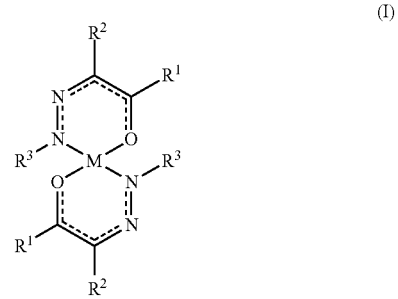

wherein
 M is a metal selected from Groups 3 through 12 of the Periodic Table;
 $R^1$ and $R^2$ are each independently H or $C_1$-$C_6$ alkyl; and
 $R^3$ is H or $C_1$-$C_8$ alkyl.

23 Claims, 11 Drawing Sheets

(56) References Cited

U.S. PATENT DOCUMENTS

| | | |
|---|---|---|
| 7,632,351 B2 | 12/2009 | Thompson |
| 2002/0013487 A1 | 1/2002 | Norman et al. |
| 2002/0098346 A1 | 7/2002 | Yitzchaik |
| 2005/0186342 A1 | 8/2005 | Sager et al. |
| 2006/0134331 A1 | 6/2006 | Thompson |
| 2006/0157863 A1 | 7/2006 | Marsh |
| 2009/0114874 A1 | 5/2009 | Norman et al. |
| 2013/0251903 A1 | 9/2013 | Han |

OTHER PUBLICATIONS

Lim, B.S. et al., "Atomic layer deposition of transition metals," Nature Materials, v. 2, Nov. 2003, pp. 749-754.

Pettinari, C. et al "Copper and silver derivatives of scorpionates and related ligands," Polyhedron 23 (2004), pp. 451-469.

Knisley, T.J. et al., "Low Temperature Growth of High Purity, Low Resistivity Copper Films by Atomic Layer Deposition," Chem. Mater. 2011, 23, pp. 4417-4419.

International Search Report dated Sep. 6, 2012 of PCT/US12/040892 filed Jun. 5, 2012, 2 pgs.

Bart, S.C. et al., "Low-Valent α-Diimine Iron Complexes for Catalytic Olefin Hydrogenation," Organometallics 2005, v. 24, pp. 5518-5527.

d'Alnoncourt, R.N. et al., "The preparation of Cu/Al2O3 catalysts via CVD in a fluidized-bed reactor," Surface and Coatings Technology 201, pp. 9035-904, 2007.

Dieck, H.T. et al., "Reaktionen von Bis(dizadien)eisen(O)," Komplexen. Chem. Ber., 120, pp. 1943-1950, Oct. 2002 (English Abstract).

Gardiner, M.G. et al., "Paramagnetic Bis(1,4-di-tert-butyl-1,4-diazabutadiene) Adducts of Lithium, Magnesium, and Zinc," Inorg. Chem. 1994, 33, pp. 2456-2461.

Ghosh, M. et al., "(α-Diimine)chromium Complexes: Molecular and Electronic Structures; a Combined Experimental and Density Functional Theoretical Study," Inorganic Chem., v. 47, n. 13, (2008), pp. 5963-5970.

Ghosh, M. et al., "A structural, spectroscopic and computational study of the molecular and electronic structure of a [bis(α-diiminato)manganese(II)] π radical complex," Dalton Trans., 2008, pp. 5149-5151.

Gong, Y. et al., "The intra-annular acylamide chelate-coordinated compound: The keto-tautomer of metal (II)-milrinone complex," J. of Molecular Structure 875 (2008), pp. 113-120.

Hassaan, "Mixed ligand complexes of bis(s-methyl-n-arylidene hydrazine carbodithioate) nickel (ii) chelates with some amino acids and nitrogenous heterocycles," J. of Islamic Academy [online] retrieved from http://www.medicaljournal-ias.org/3_4Hassaan.pdf on Jul. 1, 2010, pp. 269-272.

International Search Report dated Jul. 1, 2010 from corresponding PCT/US2010/035080 filed May 17, 2010, 2 pgs.

International Search Report for PCT/US2011/048792, Completed by the Korean Patent Office on Feb. 23, 2012, 3 pp.

International Search Report dated Aug. 17, 2012 from corresponding PCT/US12/040892 filed Jun. 5, 2012, pgs.

Kaltsoyannis, N., "Covalency in metal complexes of 1,4-diazabutadiene (dab). A density functional investigation of the electronic structures of [M(dab)2] (M = Li, Ga or Co) and [Th(NH3)NH2)3(dab)]," J. Chem. Soc., Dalton Trans., 1996, pp. 1583-1589.

Kalutarage, L.C. et al., "Low-Temperature Atomic Layer Deposition of Copper Films Using Borane Dimethylamine as the Reducing Co-reagent," Chem. Mater. 2014, 26, pp. 3731-3738.

Kalutarage, L.C. et al., "Synthesis, Structure, and Solution Reduction Reactions of Volatile and Thermally Stable Mid to Late First Row Transition Metal Complexes Containing Hydrazonate Ligands," Inorg. Chem. 2013, v. 52, pp. 5385-5394.

Kalutarage, L.C. et al., "Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films," J. Am. Chem. Soc. 2013, 135, pp. 12588-12591.

Karunarathne, M.C. et al., "Exceptional thermal stability and high volatility in mid to late first row transition metal complexes containing carboyhydrazide ligands," Polyhedron 52 (2013), pp. 820-080.

Khusniyarov, M. M. et al., "Reversible Electron Transfer Coupled to Spin Crossover in an Iron Coordination Salt in the Solid State," Angew. Chem. Int. Ed. 2008, 47, pp. 1228-1231.

Khusniyarov, M.M. et al., "Molecular and Electronic Structures of Homoleptic Nickel and Cobalt Complexes with Non-Innocent Bulky Diimine Ligands Derived from Fluorinated 1,4-Diaza-1,3-butadiene (DAD) and Bis(arylimino) acenaphthene (BIAN)," Eur. J. Inorg. Chem. 2006, pp. 2985-2996.

Khusniyarov, M.M. et al., "Tuning the Oxidation Level, the Spin State, and the Degree of Electron Delocalization In Hom- and Heteroleptic Bis(α-diimine)iron Complexes," J. Am. Chem. Soc. 2009, v. 131, pp. 1208-1221.

Knisley, T.J. et al., "Low Temperature Growth of High Purity, Low Resistivity Copper Films by Atomic Layer Deposition," Chem. Mater. 2011, v. 23, pp. 4417-4419.

Knisley, T.J. et al., "Volatility and High Thermal Stability in Mid- to Late-First-Row Transition-Metal Dizazdienyl Complexes," Organometallics 2011, v. 30, pp. 5010-5017.

Kreisel, K.A. et al., "Synthesis, Characterization, and Electronic Structure of Diimine Complexes of Chromium," Inorganic Chem., v. 74, n. 12, (2008), pp. 5293-5303.

Kreisel, K.A. et al., "The Shortest Metal-Metal Bond Yet: Molecular and Electronic Structure of a Dinuclear Chromium Diazediene Complex," J. Am. Chem. Soc. 2007, v. 129, pp. 14162-14163.

Mac-Leod-Carey, D.A. et al., "Bix[2-(2,4-dioxopentan-3-ylidene-κO)-1-(4-methoxy-phenyphydrazinato-κN1] copper(II)," Acta Cryst. 2007, E63, pp. m670-m672.

Marten, J. et al., "3-(Arylhydrazono)pentane-2,4-diones and their Complexes with Copper(II) and Nickel(II)-Synthesis and Crystal Structures," Z. Anorg. Allg. Chem. 2005, v. 631, pp. 869-877.

Muresan, N. et al., "Bis(α-diimine)iron Complexes: Electronic Structure Determination by Spectroscopy and Broken Symmetry Density Functional Theoretical Calculations," Inorganic Chem., v. 47, n. 11, (2008), pp. 4579-4590.

Muresan, N. et al., "Bis(α-diimine)nickel Complexes: Molecular and Electronic Structure of Three Members of the Electron-Transfer Series [Ni(L)2]z (z=0, 1+, 2+) (L=2-Phenyl-1,4-bis(isopropyl)-1,4-diazabutadiene). A Combined Experimental and Theoretical Study," Inorganic Chem., v. 46, n. 13, (2007) pp. 5327-5337.

Muresan, N. et al., "Neutral (bis(1,4-diaza-1,3-butadiene)nickel complexes and their corresponding monocations: molecular and electronic structures. A combined experimental and density functional theoretical study," Dalton Trans., 2007, pp. 4390-4398.

Nassimbeni, L. et al., "The Crystal and Molecular Structure of the Bis-(5-ethyl-5-isoamylbarbiturato)bis(imidazole).Complex of Nickel(II)," Acta Cryst. (1974), B30, p. 2593-2602.

Pangani et al., "Coordination compounds of lanthanides with acetylhydrazine," Inorganica Chimca Acta, v. 94,issues 1-3, Feb. 1984, Abstract p. 79.

Pettinari, C. et al, "Copper and silver derivatives of scorpionates and related ligands," Polyhedron 23 (2004), pp. 451-469.

Popoff, N. et al., "Shifting from Ziegler-Natta to Phillips-Type Catalyst? A Simple and Safe Access to Reduced Titanium Systems for Ethylene Polymerization," Macromol. Rapid Commun. 2011, 32, pp. 1921-1924.

Rijnberg et al., "A Homologous Series of Homoleptic Zinc Bis(1,4-di-tert-butyl-1,4-diaza-1,3-butadiene) Complexes: Kx(Zn(t-BuNCHCHCN-t-Bu)2 and (Zn(t-BuNCHCHN-t-Bu)2))(Otf)x (x=1,2)," Inorg. Chem. 1998, v. 37, pp. 56-63.

Robinson, M.A. et al., "Complexes Derived from Strong Field Ligands. XVII. Electronic Spectra of Octahedral Nickel(II) Complexes with Ligands of the α-Diimine and Closely Related Classes," Inorganic Chem., v. 2, n. 6, (1963), pp. 1178-1181.

Saito, T. et al., "1,4-Bis(trimethylsilyl)-,4-diaza-2,5-cyclohexadienes as Strong Salt-Free Reductants for Generating Low-Valent Early Transition Metals with Electron-Donating Ligands," J. Am. Chem. Soc. 2014, 136, pp. 5161-5170.

(56) References Cited

OTHER PUBLICATIONS

Svoboda, M. et al., "Bis(diazadien)metal(O)-Komplexe, III [1]1 Nickel(O)-bis(chelate) mit aliphatischen N-Substituenten," Z. Naturforsch. 86b, (1981), pp. 814-822 (English Abstract).

Thompson, R.K. "Amidate Complexes of the Group 4 Metals," Synthesis, Reactivity, and Hydroaminiation Catalysis. Thesis, The University of British Columbia. http://hdl.handle.net/2429/1344. Available online Nov. 8, 2008, pp. 1-120.

Tsurugi, H. et al., "Carbon Radical Generation by D0 Tantalum Complexes with α-Diimine Ligands through Ligand-Centered Redox Processes," J. Am. Chem. Soc. 2011, 133, pp. 18673-18683.

Tsurugi, H. et al., "Salt-Free Reducing Reagent of Bis(trimethylsilyl)cyclohexadiene Mediates Multielectron Reduction of Chloride Complexes of W(VI) and W(IV)," J. Am. Chem. Soc. 2013, 135, pp. 5986-5989.

Vidjayacoumar et al., "Investigation of AlMe3, BEt3, and ZnEt2 as Co-Reagents for Low Temperature Copper Metal ALD/Pulsed-CVD," Chem. Mater. 2010, v. 22, pp. 4844-4853.

Yilmaz, F. et al., "Bis-(5,5'-diethylbarbiturato) Copper(II) and Cadmium(II Complexes with Ethylenediamine. Synthesis Crystal Structures, Spectroscopic and Thermal Characterization of cis-[Cu(barb)2(en] and {[Cd(barb)2(μ-en)] -2H2O)n," Z. Anorg. Allg. Chem. 2005, v. 631, pp. 1536-1540.

Non-Final Office Action mailed Apr. 7, 2014 in U.S. Appl. No. 13/319,793, filed 100/10/2011, 7 pgs.

Non-Final Office Action mailed May 28, 2014 in U.S. Appl. No. 13/493,560, filed Jun. 11, 2012, 7 pgs.

Authors et al.: Disclosed Anonymously, IP.com Prior Art Database Technical Disclosure, IP.com No. IPCOM000173198D, Jul. 25, 2008.

Non-Final Office Action mailed Aug. 27, 2014 in U.S. Appl. No. 13/818,154, filed Feb. 21, 2013, 9 pgs.

formic acid alkyl carboxylic acid oxalic acid dicarboxylic acids sulfonic acids

HX

Inorganic Acid $H_3PO_4$ phosphoric acid $H_3PO_2$ phosphorous acid $R^4$ = H, $C_1$-$C_8$alkyl, $C_6$-$C_{12}$aryl, $C_1$-$C_8$fluoroalkyl
X = $N_3^-$, $NO_3^-$, halide(e.g., Cl, F, Br)
n = an integer from 1 to 6.

SYNTHESIS AND CHARACTERIZATION OF FIRST ROW TRANSITION METAL COMPLEXES CONTAINING α-KETO HYDRAZONATE LIGANDS AS POTENTIAL PRECURSORS FOR USE IN METAL FILM DEPOSITION

FIELD OF THE INVENTION

In at least one aspect, the present invention is related to the formation of metal films from "metalorganic" precursors.

BACKGROUND OF THE INVENTION

The growth of thin films is a central step in the fabrication of many functional materials and devices. While film growth efforts have been traditionally directed toward films greater than 100 nm, recent trends in several areas are calling for the growth of films ranging in thickness from a few atomic layers up to tens of nanometers.

In the microelectronics area, copper has replaced aluminum as the interconnect material in integrated circuits due to its lower resistivity and higher resistance to electromigration. Ultrathin (2-8 nm) manganese-silicon-oxygen layers have been proposed as replacements for existing nitride-based copper diffusion barrier layers in future devices. Since copper does not nucleate well on $SiO_2$ and other surfaces, it is difficult to deposit copper metal onto the surface features of microelectronic substrates. Accordingly, there has been considerable interest in the formation of seed layers of metals such as chromium, cobalt, and others which adhere better to substrates, and upon which copper films can be subsequently grown.

Atomic layer deposition ("ALD") is a thin film deposition technique that addresses many of the current technological demands. ALD affords inherently conformal coverage and sub-nanometer film thickness control due to its self-limited growth mechanism. In a typical ALD process, a substrate is contacted with a first chemical composition that modifies the substrate for a first predetermined period of time (a pulse). Such modification involves adsorption to the surface of the substrate, reaction with the surface of the substrate, or a combination of adsorption and reaction. A purging gas is introduced to remove any lingering first gaseous chemical composition in the vicinity of the substrate. A second gaseous chemical composition that reacts with the modified substrate surface is introduced for a second predetermined period of time into the vicinity of the substrate to form a portion of the thin film. A purging gas is subsequently introduced to remove any lingering second chemical composition in the vicinity of the substrate. These steps of contacting the substrate with the first chemical composition, purging, contacting the substrate with the second gaseous chemical composition, and purging are usually repeated a plurality of times until a film of desired thickness is coated onto the substrate. Although the prior art ALD processes work well, there is unfortunately only a limited number of chemical precursors having the requisite thermal stability, reactivity, and vapor pressure for ALD.

Accordingly, there is a need for improved methods for depositing thin films by atomic layer deposition.

SUMMARY OF THE INVENTION

The present invention solves one or more problems of the prior art by providing a compound for forming a metal-containing compound or metal-containing film or powder. The compound of this embodiment is described by formula (I):

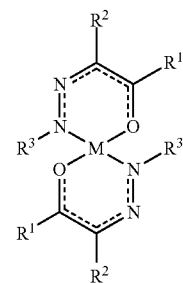

(I)

wherein
M is a metal selected from Groups 2 through 12 of the Periodic Table;
$R^1$ and $R^2$ are each independently H or $C_1$-$C_6$ alkyl; and
$R^3$ is H or $C_1$-$C_8$ alkyl.

In another embodiment, a method of preparing a compound having formula (I) as set forth above is provided. The method includes a step of reacting a group 1 metal hydrazonate salt with a metal containing compound to form the compound having formula (I).

In another embodiment, a method of forming a metal-containing product is provided. The method comprises contacting a compound having formula I as set forth above with an activating agent to form a metal-containing product.

In another embodiment, a method of forming a metal-containing film by an atomic layer deposition process is provided. The method comprises a deposition which includes contacting the substrate with vapor of a compound having formula I as set forth above such that at least a portion of the vapor of the compound having formula I adsorbs or reacts with a substrate surface to form a modified surface. The deposition cycle further includes contacting the modified surface with a vapor of an activating agent to react and form at least a portion of the metal-containing film.

In still another embodiment, a method of forming a metal-containing film on a substrate is provided. The method comprising a deposition cycle that includes contacting a substrate with a vapor of a metal-containing compound described by formula I for a first predetermined pulse time to form a first modified surface:

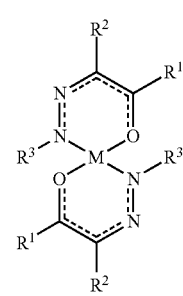

(I)

wherein:
M is a metal selected from Groups 2 to 12 of the Periodic;
$R^1$ and $R^2$ are each independently H or $C_1$-$C_6$ alkyl; and
$R^3$ is H or H or $C_1$-$C_8$ alkyl. The first modified surface is contacted with an acid for a second predetermined pulse time to form a second modified surface. The second modified surface is contacted with an activating agent for a third predetermined pulse time to form a metal layer.

BRIEF DESCRIPTION OF THE DRAWINGS

Exemplary embodiments of the present invention will become more fully understood from the detailed description and the accompanying drawings, wherein.

DESCRIPTION OF THE INVENTION

Figure 1:
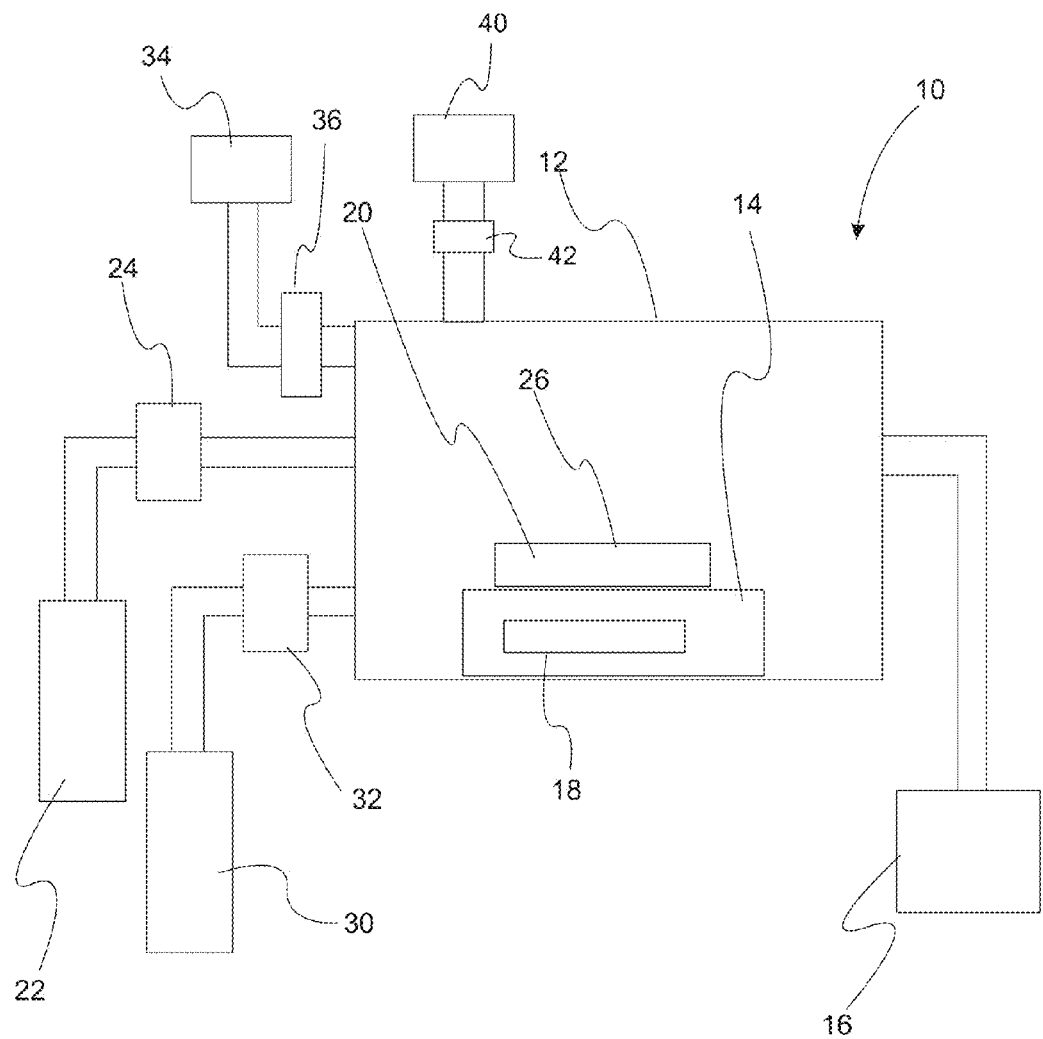
FIG. 1 is a schematic illustration of an ALD deposition system used in an embodiment of the present invention.
Figure 2:
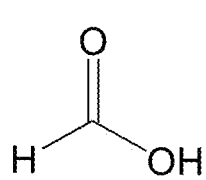
FIG. 2 provides examples of acids that can be reacted with the compounds of formula I.
Figure 2:
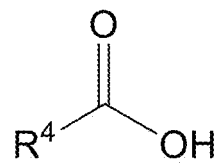
Figure 2:
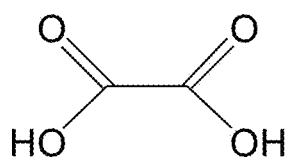
Figure 2:
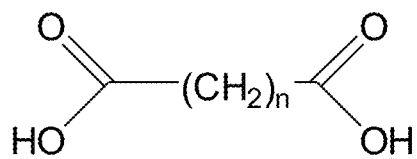
Figure 2:
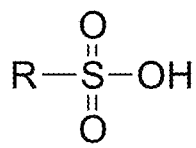
Figure 3A:
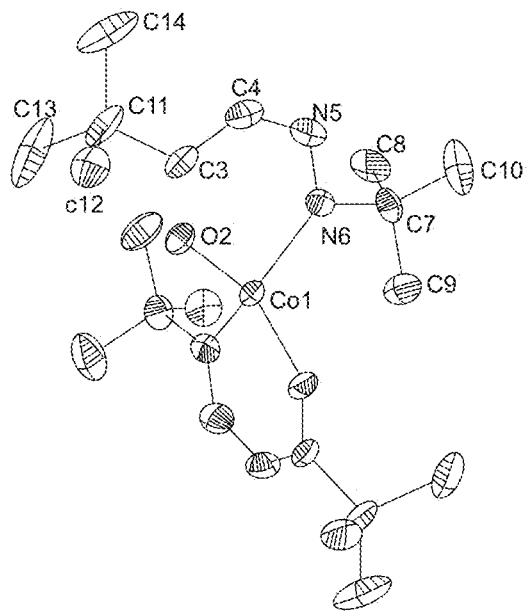
FIG. 3A provides an X-ray structure for bis((1-tert-butyl-diazenyl)-3,3-dimethylbut-1-en-2-olate)cobalt(II)
Figure 3B:
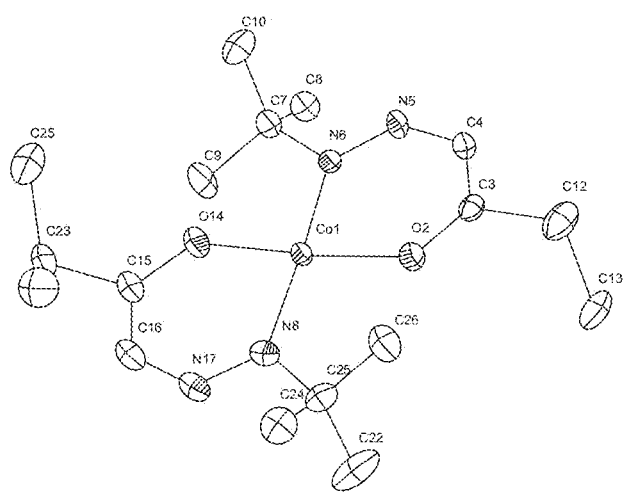
FIG. 3B provides and X-ray structure for bis((1-tert-butyl-diazenyl)-3-methylbut-1-en-2-olate)nickel(II)
Figure 3C:
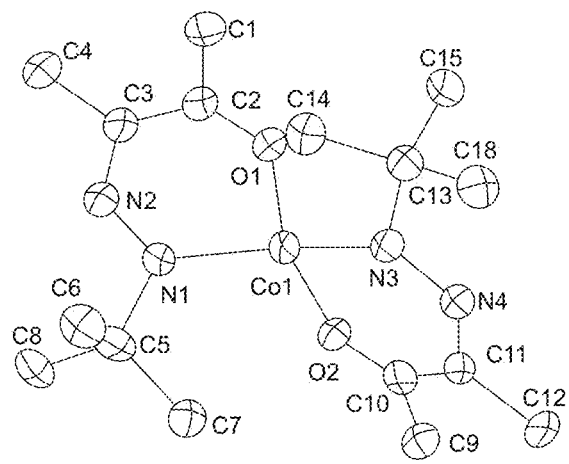
FIG. 3C provides an X-ray structure bis((3-tert-butyldiazenyl)but-2-en-2-olate)cobalt(II)
Figure 3D:
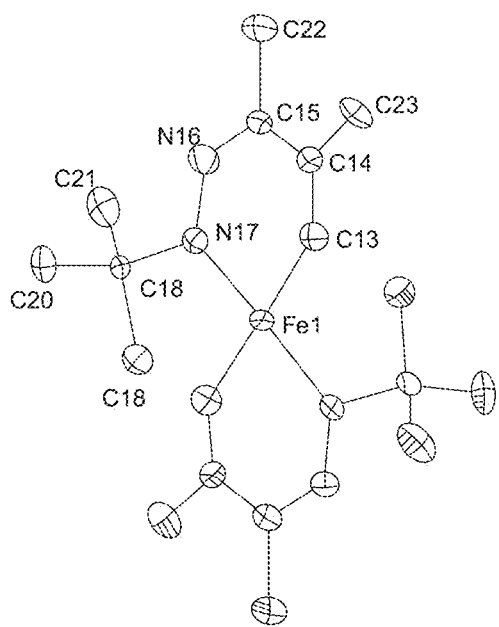
FIG. 3D provides an X-ray structure for bis((3-tert-butyl-diazenyl)but-2-en-2-olate)iron(II)

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In an embodiment, a compound that is useful for forming a metal-containing film or product is provided. The compound of this embodiment is described by formula (I):

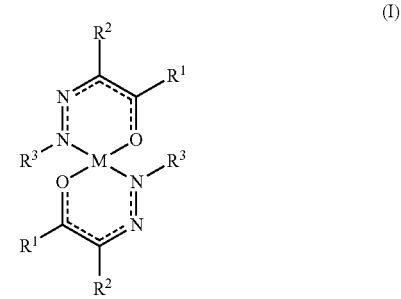

(I)

wherein

M is a metal selected from Groups 2 to 12 of the Periodic Table;

$R^1$ and $R^2$ are each independently H or $C_1$-$C_6$ alkyl; and $R^3$ is H or H or $C_1$-$C_8$ alkyl. In a refinement, $R^1$, $R^2$ and $R^3$ are each independently methyl, ethyl, n-propyl, isopropyl, n-butyl, sec-butyl, isobutyl, or t-butyl. In another refinement, M is Cr, Mn, Fe, Co, or Ni. Specific examples of compounds having formula (I) include, but are not limited to, bis((1-tert-butyldiazenyl)-3,3-dimethylbut-1-en-2-olate)chromium(II), bis((1-tert-butyldiazenyl)-3,3-dimethylbut-1-en-2-olate) manganese(II), bis((1-tert-butyldiazenyl)-3,3-dimethylbut-1-en-2-olate)iron(II), bis((1-tert-butyldiazenyl)-3,3-dimethylbut-1-en-2-olate)cobalt(II), bis((1-tert-butyldiazenyl)-3,3-dimethylbut-1-en-2-olate)nickel(II), bis((3-tert-butyldiazenyl)but-2-en-2-olate)iron(II), bis((3-tert-butyldiazenyl)but-2-en-2-olate)cobalt(II), bis((3-tert-butyldiazenyl)but-2-en-2-olate)nickel(II), and bis((1-tert-butyldiazenyl)-3-methylbut-1-en-2-olate)iron(II), bis((1-tert-butyldiazenyl)-3-methylbut-1-en-2-olate)cobalt(II), and bis((1-tert-butyldiazenyl)-3-methylbut-1-en-2-olate)nickel (II).

In another refinement of the present embodiment, a method for forming a metal is provided. In this context, the metal is characterized in having metal atoms in the zero oxidation state. The method comprises contacting a compound selected from the group of compounds having formula (I) with a compound with a reducing agent. Examples of reducing agents that can be used in this reaction include, but are not limited to, $NH_2NMe_2$, $NH_2NH_2$, $AlEt_3$, $AlMe_3$, $HSiEt_3$, LiB-$HEt_3$, $LiAlH_4$, $BH_3.N(C_2H_5)_3$, $BH_3.NH(CH_3)_2$, pinacol borane, $BH_3.S(CH_3)_2$, $BH_3.THF$, $BH_3.2$-picoline, decaborane, 9-Borabicyclo[3.3.1]nonane (9-BBN), $BH_3$.morpholine, and the like. The present refinement can be carried out either in solution or in the vapor phase (e.g. ALD, chemical vapor deposition, etc) at temperatures from about 50 to 400° C. In another refinement, the metal deposition is carried out at temperatures from about 75 to 200° C.

In a further refinement, a method of forming a metal film by an atomic layer deposition process is provided. The method comprises a deposition cycle which includes contacting the substrate with vapor of a compound having formula I as set forth above such that at least a portion of the vapor of the compound having formula I adsorbs or reacts with a substrate surface to form a modified surface. The deposition cycle further includes contacting the modified surface with a vapor of a reducing agent to react and form at least a portion of the metal film. Typically, the compound having formula I is contacted with the reducing agent at a temperature from about 50 to 400° C. Examples of reducing agents that can be used in this reaction include, but are not limited to, $NH_2NMe_2$, $NH_2NH_2$, $AlEt_3$, $AlMe_3$, $HSiEt_3$, $LiBHEt_3$, $LiAlH_4$, $BH_3.N(C_2H_5)_3$, $BH_3.NH(CH_3)_2$, pinacol borane, $BH_3.S(CH_3)_2$, $BH_3.THF$, $BH_3.2$-picoline, decaborane, 9-Borabicyclo[3.3.1]nonane (9-BBN), $BH_3$.morpholine, and the like. The present reaction is used in an ALD process as set forth below.

With reference to FIG. 1, deposition system 10 includes reaction chamber 12, substrate holder 14, and vacuum pump 16. Typically, the substrate is heated via heater 18. The method has a deposition cycle comprising contacting substrate 20 with a vapor of a metal-containing compound described by formula I as set forth above. In particular, the vapor is introduced from precursor source 22 into reaction chamber 12 for a predetermined pulse time. The pulse time is controlled via control valve 24. At least a portion of the vapor of the metal-containing compound modifies (e.g, adsorbs or reacts with) substrate surface 26 to form a modified surface. The method further comprises contacting the modified surface with a vapor of an activating agent as set forth above from source 30 for a predetermined pulse time. In a refinement, the activating agent is a reducing agent which causes the metal-containing compound to react and form at least a portion of the thin metal film on the surface of the substrate. The reduced pressure of chamber 12 is maintained by vacuum pump 16. In another refinement, the activating agent is an oxidizing agent which results in a metal oxide layer being formed. Examples of useful oxidizing agents include, but are not limited to, water, ozone, molecular oxygen, atomic oxygen, organic alcohols, hydrogen peroxide, organic hydroperoxides, organic peroxides, nitrous oxide, plasma-activated versions of the above compounds. In still another refinement, the activating agent is a nitriding agent (i.e., a nitrogen-containing compound) which results in a metal nitride layer. The pulse time is controlled via control valve 32. Examples of such nitrogen activating compounds include, but are not limited to, ammonia, hydrazine, alkyl-substituted hydrazines, and plasma activated versions thereof.

In a variation of the present embodiment, the method further comprises removing at least a portion of the vapor of the metal containing compound having formula I that is lingering in the gas phase (i.e., has not adsorbed or reacted with the substrate) from the vicinity of the substrate before introducing the vapor of the reducing agent and removing at least a portion of the vapor of the reducing agent from the vicinity of the substrate. The metal-containing compound and the reducing agent are removed in purging steps by introducing a purge gas from purge source 34 into reaction chamber 12 for a predetermined purge time. The purge time is controlled by control valve 36.

In another variation, the method further includes at least one additional deposition cycle comprising sequentially contacting the substrate with the vapor of a metal-containing compound having formula I and then the vapor of the reducing agent. In some refinements, the substrate is contacted for a plurality of additional deposition cycles. For example, the substrate may be contacted with from 1 to several thousand deposition cycles depending on the thickness of the film desired. In particular, the substrate is contacted with the vapor of a metal-containing compound having formula I and then the vapor of the reducing agent for 1 to 5000 deposition cycles. In another refinement, the substrate is contacted with the vapor of a metal-containing compound having formula I and then the vapor of the reducing agent for 10 to 2000 deposition cycles. In still another refinement, the substrate is contacted with the vapor of a metal-containing compound having formula I and then the vapor of the reducing agent for 20 to 1000 deposition cycles.

In another embodiment, a method of forming a metal-containing film is provided. With reference to FIG. 1, the vapor of a compound having formula I is introduced from precursor source 22 into reaction chamber 12 for a first predetermined pulse time. The first predetermined pulse time should be sufficiently long that available binding sites on the substrate surface (coated with metal layers or uncoated) are saturated (i.e., metal-containing compound attached). Typically, the first predetermined pulse time is from 1 second to 20 seconds. The first predetermined pulse time is controlled via control valve 24. At least a portion of the vapor of the metal-containing compound modifies (e.g, adsorbs or reacts with) substrate surface 26 to form a first modified surface. Reaction chamber 12 is then purged with an inert gas for a first purge time. The first purge time is sufficient to remove the metal-containing compound from reaction chamber 12 and is typically from 0.5 seconds to 2 minutes.

Figure 4A:
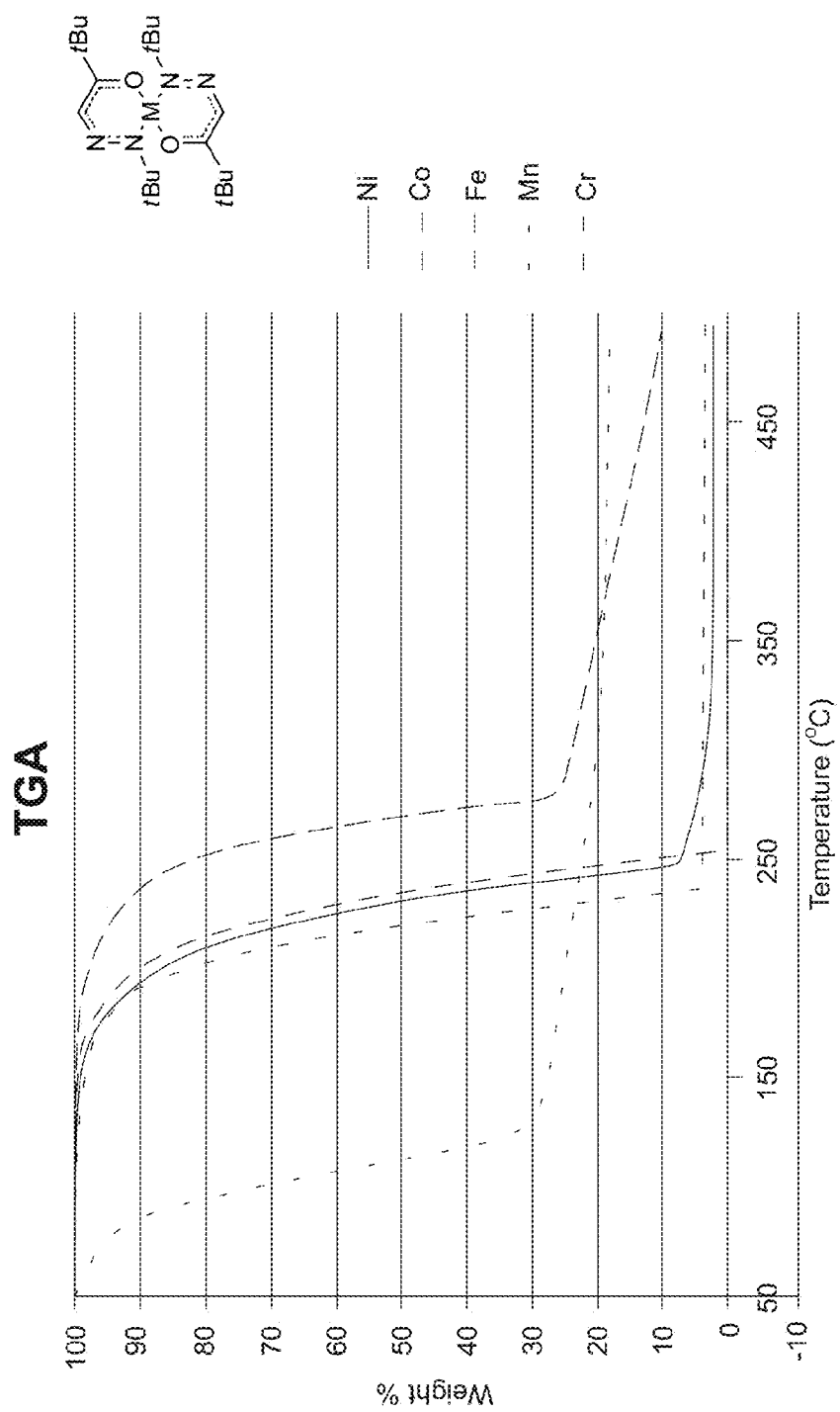
FIG. 4A provides thermogravimetric analysis (TGA) plots of compounds 1-5.
Figure 4B:
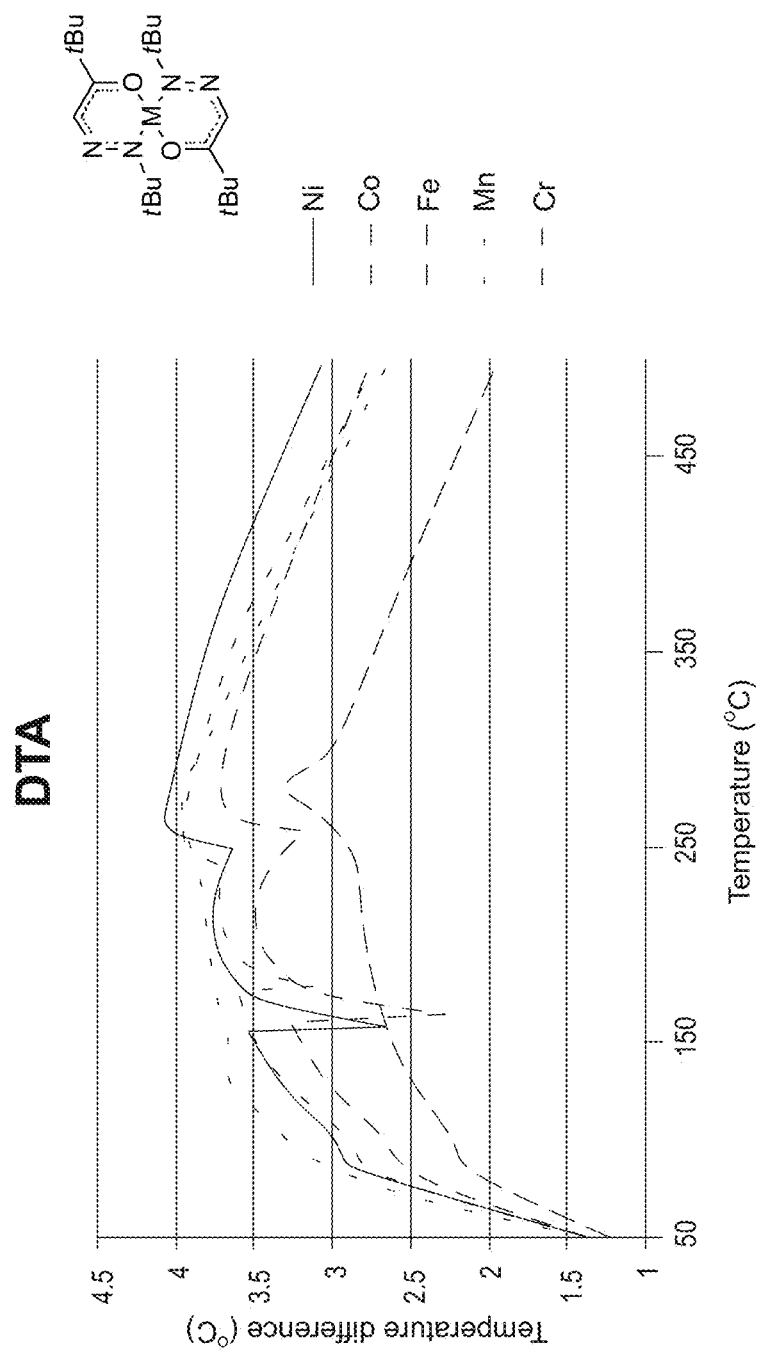
FIG. 4B provides differential thermal analysis (DTA) plots of compounds 1-5.

In the next reaction step of the deposition cycle, an acid such as formic acid is then introduced from acid source 40 into reaction chamber 12 for a second predetermined pulse time. Examples of other suitable acids are provided in FIG. 4. In FIG. 4, $R^4$ is H (i.e., hydride), $C_{1-8}$ alkyl, $C_{6-12}$ aryl, or $C_{1-8}$ fluoroalkyl, X is $N_3^-$, $NO_3^-$, halide (e.g., Cl, F, Br), and n is an integer from 1 to 6. In a refinement, $R^4$ is hydride, $C_{1-4}$ alkyl, $C_{6-10}$ aryl, or $C_{1-4}$ fluoroalkyl, X is $N_3^-$, $NO_3^-$, halide (e.g., Cl, F, Br), and n is an integer from 1 to 6. Examples of useful alkyl groups include, but are not limited to, methyl, ethyl, n-propyl, isopropyl, n-butyl, t-butyl, iso-butyl, sec-butyl, and the like. Examples of useful aryl groups include, but are not limited to, phenyl, tolyl, naphthyl, and the like. The second predetermined pulse time should be sufficiently long that available binding sites on the first modified substrate surface are saturated and a second modified surface is formed. Typically, the second predetermined pulse time is from 0.1 second to 20 seconds. The second predetermined pulse time is controlled via control valve 32. Reaction chamber 12 is then purged with an inert gas for a second purge time (typically, 0.5 seconds to 2 minutes as set forth above).

In the final reaction step of the deposition cycle, a reducing agent is then introduced from activating agent source 30 into reaction chamber 12 for a third predetermined time. In a refinement, the activating agent is an oxidizing agent, reducing agent or nitriding agent as set forth above. The third predetermined pulse time should be sufficiently long that available binding sites on the second modified substrate surface are saturated with a metal layer being formed thereon. Typically, the third predetermined pulse time is from 0.1 second to 20 seconds. Reaction chamber 12 is then purged with an inert gas for a third purge time (typically, 0.5 seconds to 2 minutes as set forth above).

During film formation by the method of the present embodiment, the substrate temperature will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

EXPERIMENTAL SECTION

General Considerations. All manipulations were carried out under argon using either Schlenk or glove box techniques. Tetrahydrofuran was distilled from sodium benzophenone ketyl, hexane was distilled from $P_2O_5$. Anhydrous transition-metal chlorides ($CrCl_2$, $MnCl_2$, $FeCl_2$, $CoCl_2$, and $NiCl_2$) were obtained from Strem Chemicals Inc. and used as received. $NiCl_2 \cdot CH_3CN$ was prepared according to a literature procedure.

$^1H$ and $^{13}C\{^1H\}$ NMR spectra were obtained at 400 and 100 MHz in benzene-$d_6$ and were referenced to the residual proton and the $^{13}C$ resonances of the solvents. IR spectra were obtained using Nujol as the medium. Melting points were determined on an Electrothermal Model 9200 melting point apparatus and are uncorrected. Thermogravimetric analyses (TGA) were carried out with a SDT-2960 TGA/DTA instrument.

Preparation of bis((1-tert-butyldiazenyl)-3,3-dimethylbut-1-en-2-olate)chromium(II) (1)

A 100 mL Schlenk flask was charged with a magnetic stir bar, 1-(2-(tert-butyl)hydrazono)-3,3-dimethylbutan-2-one (1.000 g, 5.43 mmol) and tetrahydrofuran (30 mL). To this stirred solution at ambient temperature was slowly added potassium hydride (0.239 g, 5.97 mmol), and solution was stirred for 4 h. This solution was then slowly added dropwise by cannula to a stirred suspension of anhydrous chromium(II) chloride (0.334 g, 2.71 mmol) in tetrahydrofuran (40 mL) at −78° C. The resultant dark orange solution was stirred for 15 h at ambient temperature. The volatile components were then removed under reduced pressure, and the resultant dark brown powder was dissolved in hexane (60 mL). The solution was filtered through a 1 cm pad of Celite on a coarse glass frit, and hexane was then removed under reduced pressure. Dark orange crystals of 1 were obtained by sublimation at 130° C./0.05 Torr (0.726 g, 64%): mp 274-276° C.; IR (Nujol, $cm^{-1}$) 1507 (m), 1495 (m), 1418 (m), 1364 (s), 1347 (s), 1261 (w), 1219 (w), 1183 (m), 1164 (m), 1115 (m), 1021 (w), 987 (w), 947 (w), 885 (w), 793 (w); $\mu_{eff}$=2.73 and 2.91 $\mu_B$ in the solid state and in benzene solution, respectively. Anal. Calcd for $C_{20}H_{38}CrN_4O_2$: C, 57.39; H, 9.15; N, 13.39. Found: C, 57.54; H, 9.23; N, 13.41.

Preparation of bis((1-tert-butyldiazenyl)-3,3-dimethylbut-1-en-2-olate)manganese(II) (2)

In a fashion similar to the preparation of 1, treatment of anhydrous manganese(II) chloride (0.340 g, 2.71 mmol) in tetrahydrofuran (40 mL) with a solution of potassium 1-tert-butyldiazenyl-3,3-dimethylbut-1-en-2-olate (prepared from 1-(2-(tert-butyl)hydrazono)-3,3-dimethylbutan-2-one (1.000 g, 5.43 mmol) and potassium hydride (0.239 g, 5.97 mmol) in tetrahydrofuran (30 mL)) for 15 h at ambient temperature afforded 2 (0.774 g, 68%) as dark orange crystals upon sublimation at 135° C./0.05 Torr: mp 169-171° C.; IR (Nujol, $cm^{-1}$) 1498 (m), 1484 (m), 1363 (m), 1333 (s), 1261 (m), 1220 (w), 1187 (m), 1106 (m), 1090 (w), 1031 (w), 1017 (w), 987 (w), 889 (w), 800 (w); $\mu_{eff}$=5.73 and 5.71 $\mu_B$ in the solid state and in benzene solution, respectively. Anal. Calcd for $C_{20}H_{38}MnN_4O_2$: C, 56.99; H, 9.09; N, 13.29. Found: C, 57.23; H, 9.06; N, 13.36.

Preparation of bis((1-tert-butyldiazenyl)-3,3-dimethylbut-1-en-2-olate)iron(II) (3)

In a fashion similar to the preparation of 1, treatment of anhydrous iron(II) chloride (0.349 g, 2.71 mmol) in tetrahydrofuran (40 mL) with a solution of potassium 1-tert-butyldiazenyl-3,3-dimethylbut-1-en-2-olate (prepared from 1-(2-(tert-butyl)hydrazono)-3,3-dimethylbutan-2-one (1.000 g, 5.43 mmol) and potassium hydride (0.239 g, 5.97 mmol) in tetrahydrofuran (30 mL)) for 15 h at ambient temperature afforded 3 (0.913 g, 83%) as dark orange crystals upon sublimation at 120° C./0.05 Torr: mp 177-179° C.; IR (Nujol, $cm^{-1}$) 1492 (m), 1361 (m), 1331 (s), 1264 (m), 1248 (w), 1221 (w), 1187 (m), 1109 (m), 1033 (w), 1019 (w), 991 (w), 892 (w), 822 (w), 808 (w); $\mu_{eff}$=4.82 and 4.86 $\mu_B$ in the solid state and in benzene solution, respectively. Anal. Calcd for $C_{20}H_{38}FeN_4O_2$: C, 56.87; H, 9.07; N, 13.26. Found: C, 56.78; H, 8.98; N, 13.16.

Preparation of bis((1-tert-butyldiazenyl)-3,3-dimethylbut-1-en-2-olate)cobalt(II) (4)

In a fashion similar to the preparation of 1, treatment of anhydrous cobalt(II) chloride (0.350 g, 2.71 mmol) in tetrahydrofuran (40 mL) with a solution of potassium 1-tert-butyldiazenyl-3,3-dimethylbut-1-en-2-olate (prepared from 1-(2-(tert-butyl)hydrazono)-3,3-dimethylbutan-2-one (1.000 g, 5.43 mmol) and potassium hydride (0.239 g, 5.97 mmol) in tetrahydrofuran (30 mL)) for 15 h at ambient temperature afforded 4 (0.904 g, 80%) as red crystals upon sublimation at 130° C./0.05 Torr: mp 162-164° C.; IR (Nujol, $cm^{-1}$) 1483 (m), 1462 (s), 1362 (m), 1334 (s), 1264 (m), 1248 (m), 1221 (m), 1189 (m), 1109 (m), 1033 (w), 1018 (w), 995 (w), 894 (w), 805 (m); $\mu_{eff}$=4.02 and 3.94 $\mu_B$ in the solid state and in benzene solution, respectively. Anal. Calcd for $C_{20}H_{38}CoN_4O_2$: C, 56.46; H, 9.00; N, 13.17. Found: C, 56.49; H, 8.86; N, 13.14.

Preparation of bis((1-tert-butyldiazenyl)-3,3-dimethylbut-1-en-2-olate)nickel(II) (5)

In a fashion similar to the preparation of 1, treatment of anhydrous $NiCl_2 \cdot CH_3CN$ (0.456 g, 2.71 mmol) in tetrahydrofuran (40 mL) with a solution of potassium 1-tert-butyldiazenyl-3,3-dimethylbut-1-en-2-olate (prepared from 1-(2-(tert-butyl)hydrazono)-3,3-dimethylbutan-2-one (1.000 g, 5.43 mmol) and potassium hydride (0.239 g, 5.97 mmol) in tetrahydrofuran (30 mL)) for 15 h at ambient temperature afforded 5 (0.749 g, 65%) as dark orange crystals upon sublimation at 120° C./0.05 Torr: mp 157-159° C.; IR (Nujol, cm$^{-1}$) 1485 (m), 1362 (m), 1332 (s), 1264 (m), 1246 (m), 1221 (m), 1187 (m), 1116 (m), 1034 (w), 1019 (w), 996 (w), 892 (w), 803 (w); $^1$H NMR (C$_6$D$_6$, 23° C., δ) 15.35 (s, broad, 2H, C(H)N), 5.99 (s, 18H, broad, C(CH$_3$)$_3$), −1.24 (s, broad, 18H, C(CH$_3$)$_2$); $\mu_{eff}$=2.88 and 2.93 $\mu_B$ in the solid state and in benzene solution, respectively. Anal. Calcd for C$_{20}$H$_{38}$NiN$_4$O$_2$: C, 56.49; H, 9.01; N, 13.18. Found: C, 56.49; H, 8.88; N, 13.07.

Preparation of bis((3-tert-butyldiazenyl)but-2-en-2-olate)iron(II) (6)

In a fashion similar to the preparation of 1, treatment of anhydrous iron(II) chloride (0.408 g, 3.22 mmol) in tetrahydrofuran (40 mL) with a solution of potassium 3-tert-butyldiazenylbut-2-en-2-olate (prepared from 3-(2-(tert-butyl)hydrazono)butan-2-one (1.000 g, 6.44 mmol) and potassium hydride (0.284 g, 7.08 mmol) in tetrahydrofuran (30 mL)) for 15 h at ambient temperature afforded 6 (0.313 g, 27%) as dark red crystals upon sublimation at 100° C./0.05 Torr: mp 120-122° C.; IR (Nujol, cm$^{-1}$) 1401 (m), 1361 (m), 1299 (m), 1261 (w), 1227 (w), 1188 (m), 1147 (w), 983 (w), 800 (w), 750 (w); $\mu_{eff}$=4.80 and 4.65 $\mu_B$ in the solid state and in benzene solution, respectively. Anal. Calcd for C$_{16}$H$_{30}$FeN$_4$O$_2$: C, 52.47; H, 8.26; N, 15.30. Found: C, 52.39; H, 7.99; N, 15.32.

Preparation of bis((3-tert-butyldiazenyl)but-2-en-2-olate)cobalt(II) (7)

In a fashion similar to the preparation of 1, treatment of anhydrous cobalt(II) chloride (0.418 g, 3.22 mmol) in tetrahydrofuran (40 mL) with a solution of potassium 3-tert-butyldiazenylbut-2-en-2-olate (prepared from 3-(2-(tert-butyl)hydrazono)butan-2-one (1.000 g, 6.44 mmol) and potassium hydride (0.284 g, 7.08 mmol) in tetrahydrofuran (30 mL)) for 15 h at ambient temperature afforded 7 (0.336 g, 29%) as red crystals upon sublimation at 100° C./0.05 Torr: mp 142-145° C.; IR (Nujol, cm$^{-1}$) 1494 (m), 1401 (m), 1359 (m), 1303 (s), 1262 (m), 1231 (w), 1187 (w), 1148 (m), 981 (m), 801 (w), 751 (w); $\mu_{eff}$=3.95 and 3.69 $\mu_B$ in the solid state and in benzene solution, respectively. Anal. Calcd for C$_{16}$H$_{30}$CoN$_4$O$_2$: C, 52.03; H, 8.19; N, 15.17. Found: C, 52.14; H, 8.17; N, 15.18.

Preparation of bis((3-tert-butyldiazenyl)but-2-en-2-olate)nickel(II) (8)

In a fashion similar to the preparation of 1, treatment of anhydrous NiCl$_2$.CH$_3$CN (0.543 g, 3.22 mmol) in tetrahydrofuran (40 mL) with a solution of potassium 3-tert-butyldiazenylbut-2-en-2-olate (prepared from 3-(2-(tert-butyl)hydrazono)butan-2-one (1.000 g, 6.44 mmol) and potassium hydride (0.284 g, 7.08 mmol) in tetrahydrofuran (30 mL)) for 15 h at ambient temperature afforded 8 (0.394 g, 34%) as dark orange crystals upon sublimation at 100° C./0.05 Torr: mp 120-122° C.; IR (Nujol, cm$^{-1}$) 1500 (m), 1405 (s), 1357 (s), 1302 (s), 1263 (s), 1237 (m), 1222 (m), 1185 (s), 1148 (s), 1043 (w), 980 (m), 931 (w), 805 (w), 752 (w); $^1$H NMR (C$_6$D$_6$, 23° C., δ) 68.51 (s, 6H, C(CH$_3$)O), 14.70 (s, 18H, C(CH$_3$)$_3$), −34.24 (s, 6H, C(CH)$_3$N); $\mu_{eff}$=2.75 and 2.67 $\mu_B$ in the solid state and in benzene solution, respectively. Anal. Calcd for C$_{16}$H$_{30}$NiN$_4$O$_2$: C, 52.06; H, 8.19; N, 15.18. Found: C, 52.20; H, 8.21; N, 15.06.

Preparation of bis((1-tert-butyldiazenyl)-3-methylbut-1-en-2-olate)iron(II) (9)

In a fashion similar to the preparation of 1, treatment of anhydrous iron(II) chloride (0.371 g, 2.93 mmol) in tetrahydrofuran (40 mL) with a solution of potassium 3-tert-butyldiazenylbut-2-en-2-olate (prepared from 1-(2-(tert-butyl)hydrazono)-3-methylbutan-2-one (1.000 g, 5.87 mmol) and potassium hydride (0.259 g, 6.46 mmol) in tetrahydrofuran (30 mL)) for 15 h at ambient temperature afforded 9 (0.862 g, 75%) as dark red crystals upon sublimation at 105° C./0.05 Torr: mp 114-116° C.; IR (Nujol, cm$^{-1}$) 1488 (m), 1359 (s), 1334 (m), 1302 (s), 1262 (m), 1209 (m), 1189 (m), 1114 (m), 1091 (m), 994 (w), 910 (w), 807 (m); $\mu_{eff}$=5.14 and 4.73 $\mu_B$ in the solid state and in benzene solution, respectively. Anal. Calcd for C$_{18}$H$_{34}$FeN$_4$O$_2$: C, 54.82; H, 8.69; N, 14.21. Found: C, 54.92; H, 8.58; N, 14.22.

Preparation of bis((1-tert-butyldiazenyl)-3-methylbut-1-en-2-olate)cobalt(II) (10)

In a fashion similar to the preparation of 1, treatment of anhydrous cobalt(II) chloride (0.380 g, 2.93 mmol) in tetrahydrofuran (40 mL) with a solution of potassium 3-tert-butyldiazenylbut-2-en-2-olate (prepared from 1-(2-(tert-butyl)hydrazono)-3-methylbutan-2-one (1.000 g, 5.87 mmol) and potassium hydride (0.259 g, 6.46 mmol) in tetrahydrofuran (30 mL)) for 15 h at ambient temperature afforded 10 (0.989 g, 86%) as dark red crystals upon sublimation at 100° C./0.05 Torr: mp 109-111° C.; IR (Nujol, cm$^{-1}$) 1493 (m), 1478 (m), 1364 (m), 1337 (m), 1305 (s), 1264 (w), 1219 (w), 1190 (m), 1113 (m), 1092 (m), 1048 (w), 1021 (w), 998 (w), 913 (w), 865 (w), 807 (m); $\mu_{eff}$=3.97 and 3.78 $\mu_B$ in the solid state and in benzene solution, respectively. Anal. Calcd for C$_{18}$H$_{34}$CoN$_4$O$_2$: C, 54.40; H, 8.62; N, 14.10. Found: C, 54.60; H, 8.74; N, 14.13.

Preparation of bis((1-tert-butyldiazenyl)-3-methylbut-1-en-2-olate)nickel(II) (11)

In a fashion similar to the preparation of 1, treatment of anhydrous NiCl$_2$.CH$_3$CN (0.495 g, 2.93 mmol) in tetrahydrofuran (40 mL) with a solution of potassium 3-tert-butyldiazenylbut-2-en-2-olate (prepared from 1-(2-(tert-butyl)hydrazono)-3-methylbutan-2-one (1.000 g, 5.87 mmol) and potassium hydride (0.259 g, 6.46 mmol) in tetrahydrofuran (30 mL)) for 15 h at ambient temperature afforded 11 (0.724 g, 63%) as dark orange crystals upon sublimation at 100° C./0.05 Torr: mp 92-94° C.; IR (Nujol, cm$^{-1}$) 1504 (m), 1481 (m), 1363 (s), 1338 (m), 1307 (s), 1262 (m), 1221 (w), 1190 (m), 1120 (m), 1092 (m), 1049 (w), 1022 (w), 999 (w), 802 (m); $^1$H NMR (C$_6$D$_6$, 23° C., δ) 16.22 (s, broad) 4.74 (s, broad); $\mu_{eff}$=3.00 and 3.01 $\mu_B$ in the solid state and in benzene solution, respectively. Anal. Calcd for C$_{18}$H$_{34}$NiN$_4$O$_2$: C, 54.43; H, 8.63; N, 14.11. Found: C, 54.63; H, 8.55; N, 14.12.

The following reaction scheme shows the synthesis of α-keto hydrazonate transition metal complexes.

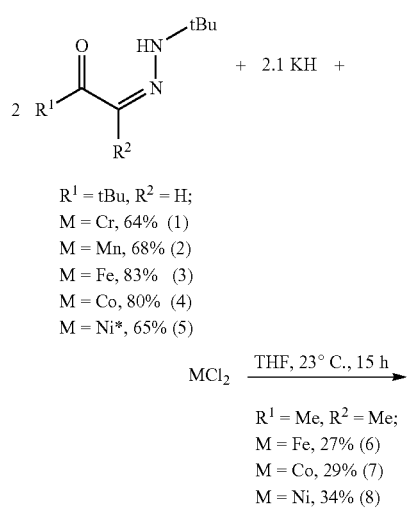

R¹ = tBu, R² = H;
M = Cr, 64% (1)
M = Mn, 68% (2)
M = Fe, 83% (3)
M = Co, 80% (4)
M = Ni*, 65% (5)

MCl₂ —THF, 23° C., 15 h→

R¹ = Me, R² = Me;
M = Fe, 27% (6)
M = Co, 29% (7)
M = Ni, 34% (8)

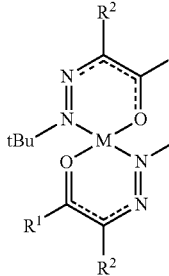

R¹ = iPr, R² = H;
M = Fe, 75% (9)
M = Co, 86% (10)
M = Ni, 63% (11)

*NiCl₂(CH₃CN) was used

Cr, Mn, Fe, Co, Ni,

Structural Analysis

X-ray structural analyses show tetrahedral, monomeric complexes. Bond lengths show that the anion is delocalized, which increases the thermal stability of complexes.

These metal complexes sublime in the range of 100-135° C. at 0.05 Torr and decompose within the temperature range of 235-310° C. as illustrated by Table 1.

TABLE 1

Thermal properties of the complexes.

| Compound | Isolated yield by sublimation % | Sublimation temperature (° C.) | Melting point (° C.) | Decomposition temperature (° C.) |
| --- | --- | --- | --- | --- |
| 1 | 64 | 130 | 274-276 | 278 |
| 2 | 68 | 135 | 169-171 | 257 |
| 3 | 83 | 120 | 177-179 | 241 |
| 4 | 80 | 130 | 162-164 | 260 |
| 5 | 65 | 120 | 157-159 | 245 |
| 6 | 27 | 100 | 120-122 | 250 |
| 7 | 29 | 100 | 142-145 | 250 |
| 8 | 34 | 100 | 133-135 | 235 |
| 9 | 75 | 105 | 114-116 | 307 |
| 10 | 86 | 100 | 109-111 | 301-308 |
| 11 | 63 | 100 | 92-94 | 268-273 |

Preparative sublimation studies were carried out to get more insight about volatility of the complexes. In preparative sublimations, 0.5 g samples were sublimed at 0.05 Torr and the temperature was adjusted so that the sublimation was complete in less than 3-4 h. Preparative sublimation temperatures approximate the temperature required to deliver the precursors to ALD reactor. Table 2 shows preparative sublimation temperatures, recovered percentages, and residue percentages.

TABLE 2

Preparative sublimation information of the complexes.

| Compound | Recovered % | Residue % | Sub: Temperature (° C.) |
| --- | --- | --- | --- |
| 1 | 96 | 3 | 130 |
| 2 | 95 | 2 | 135 |
| 3 | 99 | <1 | 120 |
| 4 | 99 | <1 | 130 |
| 5 | 97 | 2 | 120 |
| 6 | 97 | 2 | 100 |
| 7 | 98 | 2 | 100 |
| 8 | 98 | 1 | 100 |
| 9 | 97 | <1 | 105 |
| 10 | 97 | <1 | 100 |
| 11 | 96 | <1 | 100 |

Figure 5A:
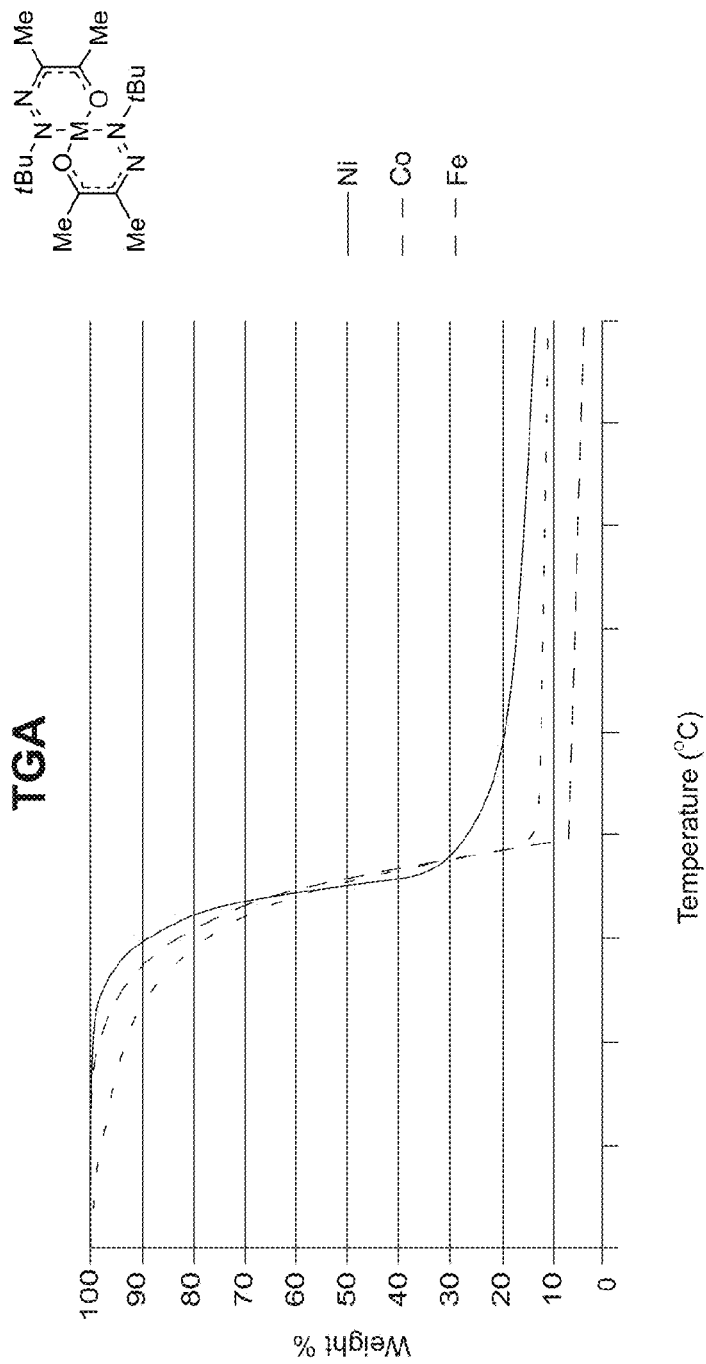
FIG. 5A provides TGA plots of compounds 6-8.
Figure 5B:
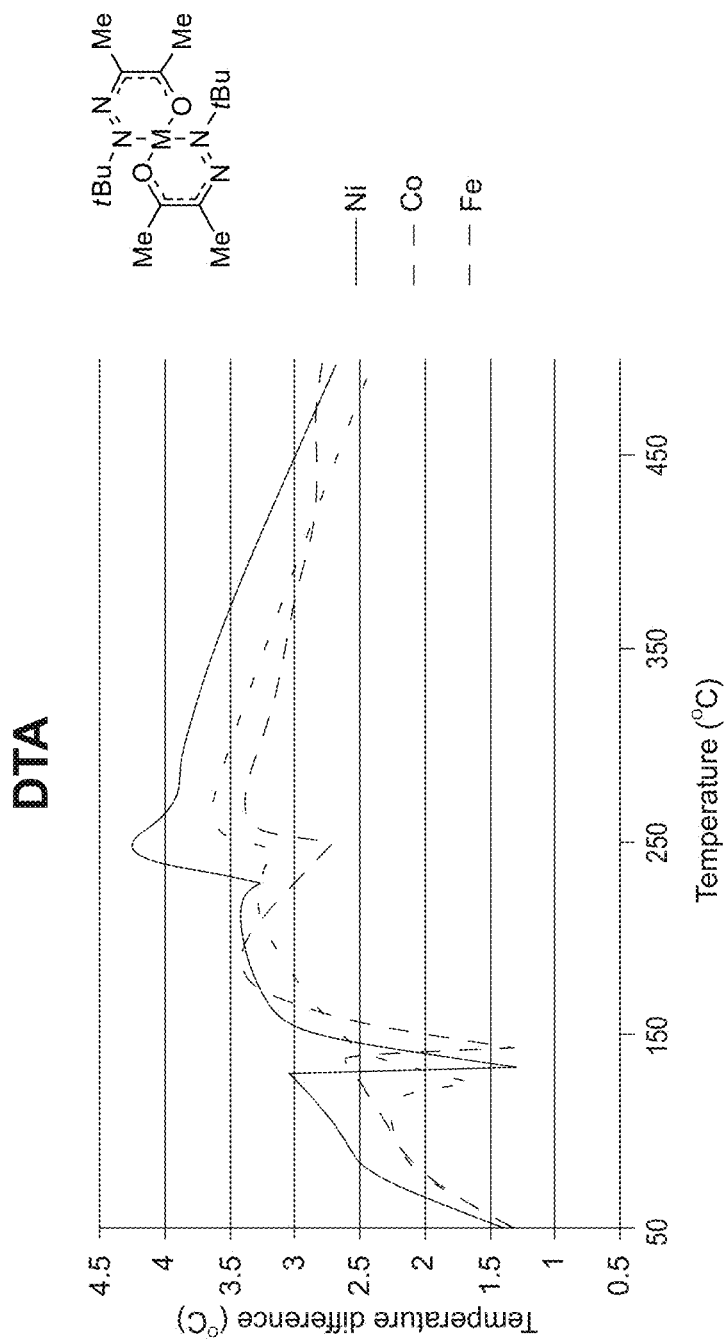
FIG. 5B provides DTA plots of compounds 6-8.
Figure 6A:
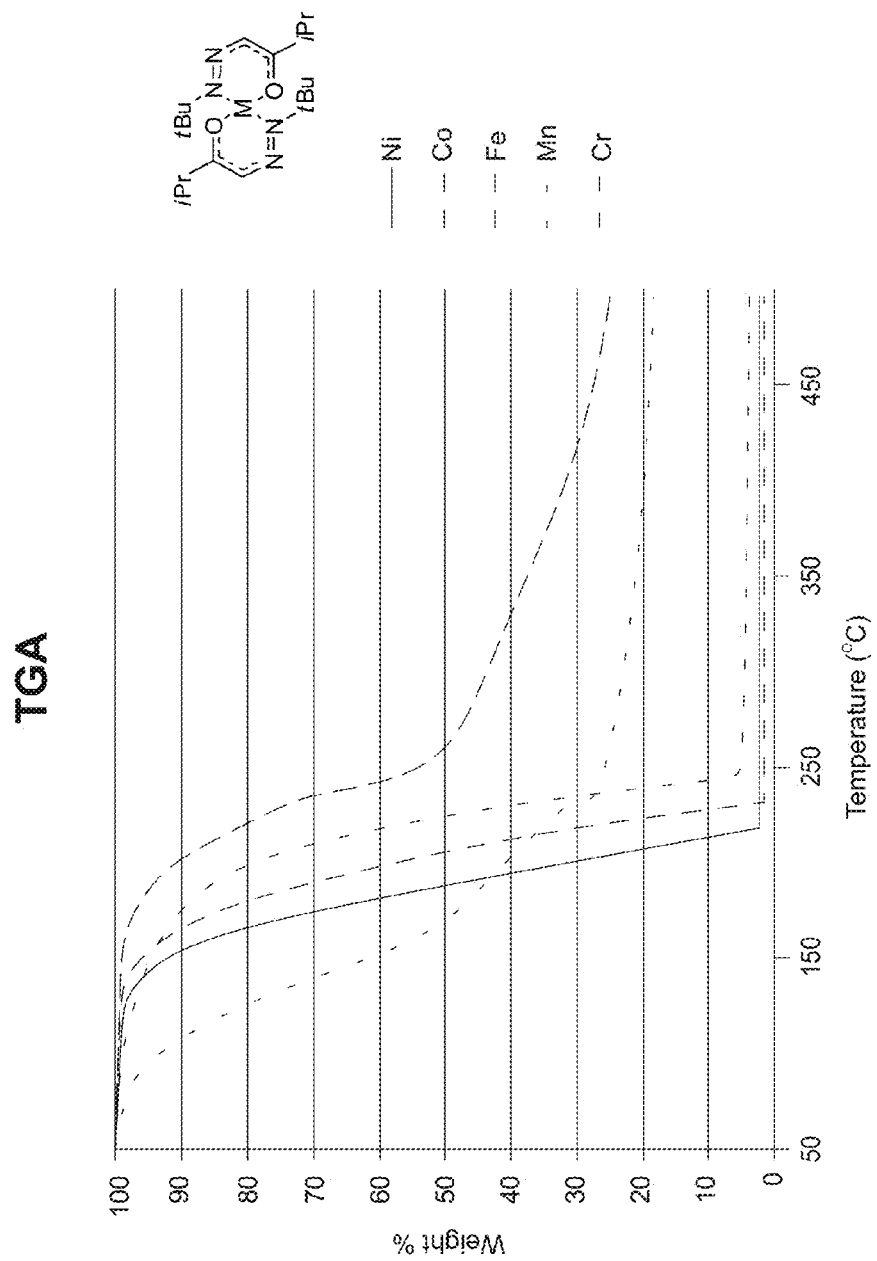
FIG. 6A provides TGA plots of compounds 9-11.
Figure 6B:
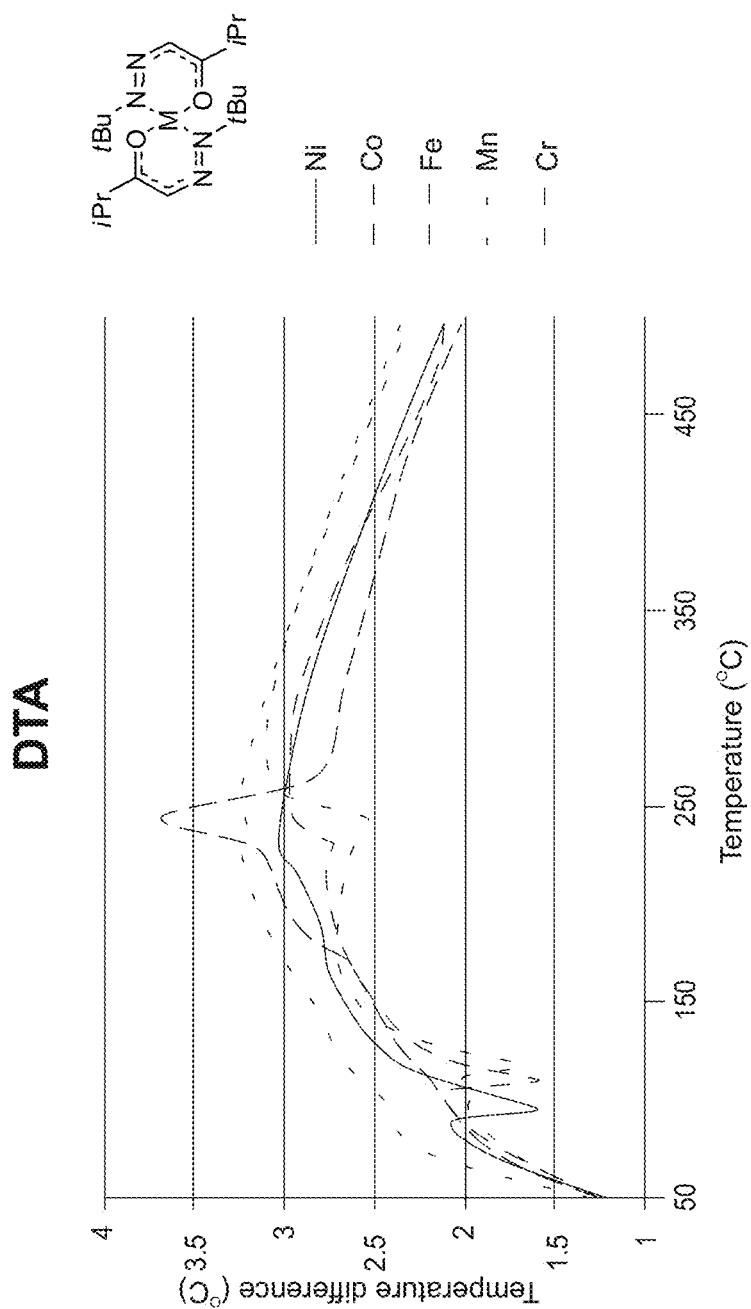
FIG. 6B provides DTA plots of compounds 9-11.
Figure 7:
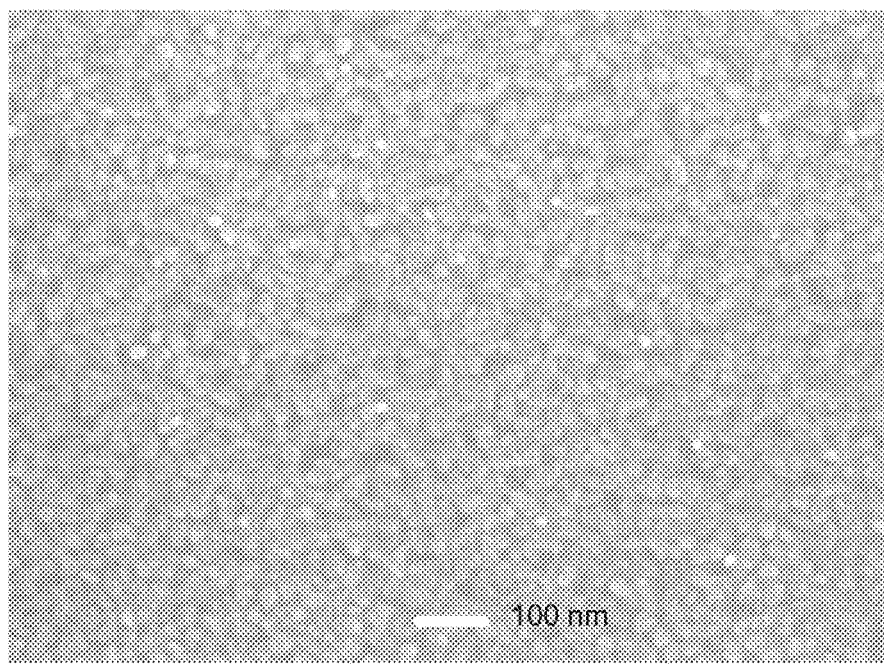
FIG. 7 provides an SEM image showing a film formed from bis((1-tert-butyldiazenyl)-3,3-dimethylbut-1-en-2-olate)cobalt(II)

TGA (thermogravimetric analysis) and DTA (differential thermal analysis) was carried out for all complexes and TGA traces for 1-11 are shown in FIGS. 3-8. FIG. 3 provides TGA plots of compounds 1-5. FIG. 4 provides DTA plots of compounds 1-5. FIG. 5 provides TGA plots of compounds 6-8. FIG. 6 provides DTA plots of compounds 6-8. FIG. 7 provides TGA plots of compounds 9-11. FIG. 8 provides DTA plots of compounds 9-11. All complexes show single weight losses. TGA traces of manganese and chromium complexes do not afford good data because of their high air sensitivity and TGA requires exposure of the sample to air during sample transfer to TGA/DTA sample pan.

Solution phase reactions were carried out with available co-reagents to observe the reactivity of precursors. Hydrazine reacts with 4 to give black powder and it sticks to stir bar, which shows that the powder is magnetic. Since the cobalt metal is magnetic, this observation demonstrates that 4 can be used to deposit cobalt metal films. Brown and black solutions or powders that have been obtained by other reactions may be due to the formation of metal nanoparticles.

ALD studies were carried out for complex 4 with anhydrous hydrazine in order to deposit cobalt metal films. For these ALD studies, pulse and purge times are as follows: i) Precursor pulse time 3.0 seconds, ii) Precursor purge time 5.0 seconds, iii) co-reagent pulse time 0.2 seconds, and iv) co-reagent purge time 5.0 seconds. Substrates for the study are Ru, Pd, Pt, Si with native oxide, and H-terminated Si. A total of 1000 cycles are used with deposition studies carried out at 200° C. Films are observed visually on Ru substrates. SEM and XRD were taken. FIG. 6 provides an SEM image showing a very thin film (ca. 8 nm) formed at 200° C. on Ru from compound 4.

What is claimed is:

1. A compound having formula (I):

(I)

[chemical structure]

wherein
M is a metal selected from Groups 2 to 12 of the Periodic Table;
R¹ and R² are each independently H or $C_1$-$C_6$ alkyl; and
R³ is H or H or $C_1$-$C_8$ alkyl.

2. The compound of claim 1 wherein M is Cr, Mn, Fe, Co, or Ni.

3. The compound of claim 2 wherein R¹, R², and R³ are each independently methyl, ethyl, n-propyl, isopropyl, n-butyl, sec-butyl, isobutyl, or t-butyl.

4. The compound of claim 1 selected from the group consisting of bis((1-tert-butyldiazenyl)-3,3-dimethylbut-1-en-2-olate)chromium(II), bis((1-tert-butyldiazenyl)-3,3-dimethylbut-1-en-2-olate)manganese(II), bis((1-tert-butyldiazenyl)-3,3-dimethylbut-1-en-2-olate)iron(II), bis((1-tert-butyldiazenyl)-3,3-dimethylbut-1-en-2-olate)cobalt(II), bis((1-tert-butyldiazenyl)-3,3-dimethylbut-1-en-2-olate)nickel(II), bis((3-tert-butyldiazenyl)but-2-en-2-olate)iron(II), bis((3-tert-butyldiazenyl)but-2-en-2-olate)cobalt(II), bis((3-tert-butyldiazenyl)but-2-en-2-olate)nickel(II), and bis((1-tert-butyldiazenyl)-3-methylbut-1-en-2-olate)iron(II), bis((1-tert-butyldiazenyl)-3-methylbut-1-en-2-olate)cobalt(II), and bis((1-tert-butyldiazenyl)-3-methylbut-1-en-2-olate)nickel(II).

5. A method for forming a metal-containing film, the method comprising contacting a compound having formula I with an activating agent to form the metal-containing film:

(I)

[chemical structure]

wherein
M is a metal selected from Groups 2 to 12 of the Periodic; and
R¹ and R² are each independently H or $C_1$-$C_6$ alkyl; and
R³ is H or H or $C_1$-$C_8$ alkyl.

6. The method of claim 5 wherein the activating agent is a reducing agent.

7. The method of claim 6 wherein the reducing agent is selected from the group consisting of $NH_2NMe_2$, $NH_2NH_2$, $AlEt_3$, $AlMe_3$, $HSiEt_3$, $LiBHEt_3$, $LiAlH_4$, $BH_3.N(C_2H_5)_3$, $BH_3.NH(CH_3)_2$, pinacol borane, $BH_3.S(CH_3)_2$, $BH_3.THF$, $BH_3$.2-picoline, decaborane, 9-Borabicyclo[3.3.1]nonane (9-BBN), $BH_3$.morpholine, and combinations thereof.

8. The method of claim 5 wherein the activating agent is an oxidizing agent or a nitriding agent.

9. The method of claim 5 wherein M is Cr, Mn, Fe, Co, or Ni.

10. The method of claim 5 wherein R¹ and R² are each independently methyl, ethyl, n-propyl, isopropyl, n-butyl, sec-butyl, isobutyl, or t-butyl.

11. The method of claim 10 wherein a substrate is contacted with a vapor of the compound having formula (I) to form a modified substrate surface during a first deposition cycle.

12. The method of claim 11 further comprising contacting the modified surface with a reducing agent to form a metal film disposed over the substrate during the first deposition cycle.

13. The method of claim 12 wherein the substrate is additionally contacted with the vapor of the compound having formula (I) and then the vapor of a reducing agent during a plurality of additional deposition cycles.

14. The method of claim 13 wherein the substrate is coated with from 1 to 5000 deposition cycles.

15. The method of claim 14 wherein the substrate is coated at a temperature from about 50 to 400° C.

16. The method of claim 15 wherein the substrate is contacted with a purge gas after contacting the substrate with the vapor of the compound having formula (I) and before contacting the substrate with the vapor of the reducing agent.

17. The method of claim 16 wherein the substrate is contacted with the purge gas after contacting the substrate with the vapor of the reducing agent and before a subsequent step of contacting the vapor of the compound.

18. The method of claim 5 wherein the compound having formula (I) is selected from the group consisting of bis((1-tert-butyldiazenyl)-3,3-dimethylbut-1-en-2-olate)chromium (II), bis((1-tert-butyldiazenyl)-3,3-dimethylbut-1-en-2-olate)manganese(II), bis((1-tert-butyldiazenyl)-3,3-dimethylbut-1-en-2-olate)iron(II), bis((1-tert-butyldiazenyl)-3,3-dimethylbut-1-en-2-olate)cobalt(II), bis((1-tert-butyldiazenyl)-3,3-dimethylbut-1-en-2-olate)nickel (II), bis((3-tert-butyldiazenyl)but-2-en-2-olate)iron(II), bis((3-tert-butyldiazenyl)but-2-en-2-olate)cobalt(II), bis((3-tert-butyldiazenyl)but-2-en-2-olate)nickel(II), and bis((1-tert-butyldiazenyl)-3-methylbut-1-en-2-olate)iron(II), bis((1-tert-butyldiazenyl)-3-methylbut-1-en-2-olate)cobalt(II), and bis((1-tert-butyldiazenyl)-3-methylbut-1-en-2-olate)nickel(II).

19. A method of preparing a compound having formula (I):

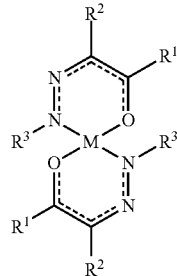

(I)

wherein
M is a metal selected from Groups 2 to 12 of the Periodic Table; and
$R^1$ and $R^2$ are each independently H or $C_1$-$C_6$ alkyl; and
$R^3$ is H or H or $C_1$-$C_8$ alkyl,
the method comprising reacting a group 1 metal hydrazonate salt with a metal containing compound to form the compound having formula (I).

20. The method of claim 19 wherein M is Cr, Mn, Fe, Co, or Ni.

21. The method of claim 20 wherein $R^1$ and $R^2$ are each independently methyl, ethyl, n-propyl, isopropyl, n-butyl, sec-butyl, isobutyl, or t-butyl.

22. The method of claim 17 wherein the compound having formula (I) is selected from the group consisting of bis((1-tert-butyldiazenyl)-3,3-dimethylbut-1-en-2-olate)chromium (II), bis((1-tert-butyldiazenyl)-3,3-dimethylbut-1-en-2-olate)manganese(II), bis((1-tert-butyldiazenyl)-3,3-dimethylbut-1-en-2-olate)iron(II), bis((1-tert-butyldiazenyl)-3,3-dimethylbut-1-en-2-olate)cobalt(II), bis((1-tert-butyldiazenyl)-3,3-dimethylbut-1-en-2-olate)nickel (II), bis((3-tert-butyldiazenyl)but-2-en-2-olate)iron(II), bis ((3-tert-butyldiazenyl)but-2-en-2-olate)cobalt(II), bis((3-tert-butyldiazenyl)but-2-en-2-olate)nickel(II), and bis((1-tert-butyldiazenyl)-3-methylbut-1-en-2-olate)iron(II), bis ((1-tert-butyldiazenyl)-3-methylbut-1-en-2-olate)cobalt(II), and bis((1-tert-butyldiazenyl)-3-methylbut-1-en-2-olate) nickel(II).

23. A method of forming a metal film on a substrate, the method comprising a deposition cycle including:
a) contacting a substrate with a vapor of a metal-containing compound described by formula I for a first predetermined pulse time to form a first modified surface:

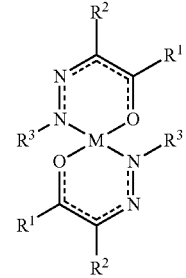

(I)

wherein:
M is a metal selected from Groups 2 to 12 of the Periodic; and
$R^1$ and $R^2$ are each independently H or $C_1$-$C_6$ alkyl; and
$R^3$ is H or H or $C_1$-$C_8$ alkyl;
b) contacting the first modified surface with an acid for a second predetermined pulse time to form a second modified surface; and
c) contacting the second modified surface with an activating agent for a third predetermined pulse time to form a metal layer.

* * * * *

UNITED STATES PATENT AND TRADEMARK OFFICE
CERTIFICATE OF CORRECTION

PATENT NO.         : 8,907,115 B2                                    Page 1 of 1
APPLICATION NO.    : 13/709564
DATED              : December 9, 2014
INVENTOR(S)        : Charles H. Winter et al.

It is certified that error appears in the above-identified patent and that said Letters Patent is hereby corrected as shown below:

Claims

Column 13, line 29, claim 1:     delete "H or" (first occurrence)

Column 14, line 6, claim 5:      delete "H or" (first occurrence)

Column 15, line 21, claim 19:    delete "H or" (first occurrence)

Column 16, line 31, claim 23:    delete "H or" (first occurrence)

Signed and Sealed this
Sixth Day of October, 2015

Michelle K. Lee
*Director of the United States Patent and Trademark Office*